US009936308B2

United States Patent
Harczos

(10) Patent No.: US 9,936,308 B2
(45) Date of Patent: Apr. 3, 2018

(54) HEARING AID APPARATUS WITH FUNDAMENTAL FREQUENCY MODIFICATION

(71) Applicant: Fraunhofer-Gesellschaft zur Foerderung der angewandten Forschung e.v., Munich (DE)

(72) Inventor: Tamas Harczos, Wolfsberg OT Wuembach (DE)

(73) Assignee: Fraunhofer-Gesellschaft zur Foerderung der angewandten Forschung e.v., Munich (DE)

( * ) Notice: Subject to any disclaimer, the term of this patent is extended or adjusted under 35 U.S.C. 154(b) by 0 days.

(21) Appl. No.: 15/156,037

(22) Filed: May 16, 2016

(65) Prior Publication Data
US 2016/0261959 A1    Sep. 8, 2016

Related U.S. Application Data

(63) Continuation of application No. PCT/EP2014/074258, filed on Nov. 11, 2014.

(30) Foreign Application Priority Data

Nov. 28, 2013  (DE) .................. 10 2013 224 417

(51) Int. Cl.
*G10L 21/003*    (2013.01)
*H04R 25/00*    (2006.01)
(Continued)

(52) U.S. Cl.
CPC .......... *H04R 25/353* (2013.01); *G10L 21/013* (2013.01); *A61N 1/36032* (2013.01); *H04R 2225/43* (2013.01)

(58) Field of Classification Search
CPC ....... G10L 21/003; G10L 21/00; G10L 21/01; G10L 21/013; G10L 2021/003;
(Continued)

(56) References Cited

U.S. PATENT DOCUMENTS

| 5,729,694 A * | 3/1998 | Holzrichter ............. G10L 15/24 704/270 |
| 7,219,059 B2 * | 5/2007 | Gupta .................... G09B 19/06 704/238 |
| 2010/0211395 A1 * | 8/2010 | Beerends ................ G10L 25/69 704/270 |

FOREIGN PATENT DOCUMENTS

| CN | 102779526 A | 11/2012 |
| EP | 1973101 A1 | 9/2008 |

(Continued)

OTHER PUBLICATIONS

Office Action issued in parallel Japanese Patent App. No. 2016-532612 dated Apr. 27, 2017 (10 pages with English translation).
(Continued)

*Primary Examiner* — Qi Han
(74) *Attorney, Agent, or Firm* — Haynes and Boone, LLP; Robert P. Ziemian

(57) ABSTRACT

A hearing aid apparatus includes a frequency analysis device configured to determine an instantaneous fundamental frequency value of a speech signal for a time portion of the speech signal. A statistical evaluation device is configured to determine an average fundamental frequency value of the speech signal over several time portions. A hearing aid apparatus further includes a fundamental frequency modifier that is configured to modify the instantaneous fundamental frequency value to a modified fundamental frequency value such that a difference or a quotient of the instantaneous fundamental frequency value is changed to the average fundamental frequency value according to a specific func-
(Continued)

tion. Thereby, a frequency range may be modified within which the fundamental frequency value varies. The hearing aid apparatus further includes a speech signal generator that is configured to generate, on the basis of the modified fundamental frequency value, a speech signal modified with regard to the fundamental frequency.

12 Claims, 7 Drawing Sheets

(51) Int. Cl.
*G10L 21/013* (2013.01)
*A61N 1/36* (2006.01)

(58) Field of Classification Search
CPC ........... G10L 2021/00; G10L 2021/013; G10L 2021/02; G10L 2021/06; G10L 2021/065
USPC ................ 704/207, 206, 205, 209, 219, 220
See application file for complete search history.

(56) References Cited

FOREIGN PATENT DOCUMENTS

| JP | 2008040431 A | 2/2008 |
|---|---|---|
| JP | 2008152042 A | 7/2008 |
| JP | 2012037726 A | 2/2012 |
| JP | 2013101212 A | 5/2013 |
| JP | 2013117556 A | 6/2013 |

OTHER PUBLICATIONS

Stephan M. Bernsee, "Pitch Shifting Using the Fourier Transform," The DSP Dimension, http://blogs.zynaptiz.com/bernsee/pitch-shifting-using-the-ft/, Sep. 21, 1999, 8 pages.
A.R. Moller, "Cochlear and Brainstem Implants," Advances in Oto-Rhino-Laryngology, vol. 64, S. Karger AG 2006, 237 pages.
"Cochlear Implants," http://web.archive.org/web/20131004082606/http://www.hearinglink.org/cochlearimpla..., printed Jun. 1, 2016, 3 pages.
Douglas O'Shaughnessy, "Linear Predictive Coding. One Popular Technique of Analyzing Certain Physical Signals," IEEE Potentials, Feb. 1988, pp. 29-32.
"Deafness and Hearing Loss," WHO Fact sheet No. 300, updated Mar. 2015, http://www.who.int/mediacentre/factsheets/fs300/en/, 5 pages.
Rao, et al., "Prosody Modification Using Instants of Significant Excitation," IEEE Transactions on Audio, Speech, and Language Processing, vol. 14, No. 3, May 2006, pp. 972-980.
Chattergee, et al., "Processing F0 with cochlear implants: Modulation frequency discrimination and speech intonation recognition," Hearing Research 235 (2008), pp. 143-156.
Meister et al., "The perception of prosody and speaker gender in normal-hearing listeners and cochlear implant recipients," International Journal of Audiology, 2009, 48:38-48.

* cited by examiner

HEARING AID APPARATUS WITH FUNDAMENTAL FREQUENCY MODIFICATION

CROSS-REFERENCE TO RELATED APPLICATIONS

This application is a continuation of copending International Application No. PCT/EP2014/074258, filed Nov. 11, 2014, which is incorporated herein by reference in its entirety, and additionally claims priority from German Application No. 102013224417.7, filed Nov. 28, 2013, which is incorporated herein by reference in its entirety.

Embodiments of the present invention relate to a hearing aid apparatus. Further embodiments of the present invention relate to a method for processing a speech signal. Further embodiments relate to a computer program for executing the method for processing a speech signal on a computer, by means of a processor, a microcontroller or a comparable apparatus. Further embodiments relate to tone range extension or pitch range broadening for hearing aids and implantable auditory prostheses in order to improve the perception of prosodic features of language.

BACKGROUND OF THE INVENTION

It is estimated that until now (November 2013) approximately 250,000 people worldwide have received cochlear implants. Cochlear implants are the most common form of implantable auditory prostheses. Cochlear implants enable people with moderate to severe sensorineural hearing disability to perceive sound, and provide sufficient auditory information in order to enable fairly sufficient listening comprehension in a quiet environment. During implantation, an electrode array is introduced into the cochlea which stimulates the auditory nerve by means of electrical impulses. In the case of the auditory nerve being damaged, a brain stem implant whose functionality is very similar to that of a cochlear implant is a better choice than an implantable auditory prosthesis. Regarding speech perception, however, brain stem implants usually are not able to achieve the efficiency of cochlear implants.

In contrast to electrode arrays that are used in implantable auditory prostheses, where each electrode corresponds to a specific frequency band, an intact cochlea comprises more than 3,000 inner hair cells, which enables much better frequency resolution (compared to the approximately 10-50 electrodes or frequency bands of common cochlear implants).

Apart from the users of implantable auditory prostheses (implanted auditory prostheses), approximately 40 million people with low-level to severe hearing loss use non-implanted hearing aids. While hearing aids in specific cases (mainly in conjunction with low-scale hearing loss) are able to restore the hearing capability at a high level, in most cases hearing supported by hearing aids still lags behind normal hearing.

Currently, speech processors for hearing aids, cochlear implants and brain stem implants use a multitude of pre-processing algorithms including automatic gain and sensitivity control, optimization of the dynamic range, background noise reduction, wind noise reduction, etc. Today, treatment by means of hearing aids and implantable auditory prostheses focuses on improving the perception of words and sentences. However, picking up (accompanying) information such as intonation is reduced for hearing aid users and often is not perceivable for implant users. As a consequence, these users are not able to perceive important elements of background information coded into prosody, or emotions linguistically expressed by the speaker. Often, implant users are not even able to determine if a sentence is a question or a statement, which may lead to uncertainties and social isolation.

It is the object of the present invention to improve the perception of linguistic background information such as prosody and/or emotions for hearing aid users and, in doing so, to improve participation in conversations with other people.

SUMMARY

According to an embodiment, a hearing aid apparatus may have: a frequency analysis device that is configured to determine an instantaneous fundamental frequency value of a speech signal for a time portion of the speech signal; a statistical evaluation device that is configured to determine an average fundamental frequency value of the speech signal over several time portions; a fundamental frequency modifier that is configured to modify the instantaneous fundamental frequency value to a modified fundamental frequency value such that a difference or a quotient of the instantaneous fundamental frequency value is changed to the average fundamental frequency value according to a specific function, in order to thus modify a frequency range within which the fundamental frequency value varies; and a speech signal generator that is configured to generate, on the basis of the modified fundamental frequency value, a speech signal modified with regard to the fundamental frequency.

According to another embodiment, a method for processing a speech signal may have the steps of: determining an instantaneous fundamental frequency value of a speech signal for a time portion of the speech signal; determining an average fundamental frequency value of the speech signal over several time portions; modifying the instantaneous fundamental frequency value to a modified fundamental frequency value such that a difference or a quotient of the instantaneous fundamental frequency value is changed to the average fundamental frequency value according to a specific function in order to modify a frequency range within which the fundamental frequency value varies; and generating, on the basis of the modified fundamental frequency value, a speech signal modified with regard to the fundamental frequency.

According to another embodiment, a non-transitory digital storage medium may have a computer program stored thereon to perform the method for processing a speech signal, which method may have the steps of:

i. determining an instantaneous fundamental frequency value of a speech signal for a time portion of the speech signal;

ii. determining an average fundamental frequency value of the speech signal over several time portions;

iii. modifying the instantaneous fundamental frequency value to a modified fundamental frequency value such that a difference or a quotient of the instantaneous fundamental frequency value is changed to the average fundamental frequency value according to a specific function in order to modify a frequency range within which the fundamental frequency value varies; and iv. generating, on the basis of the modified fundamental frequency value, a speech signal modified with regard to the fundamental frequency;

v. when said computer program is run by a computer.

Embodiments of the present invention provide a hearing aid apparatus having a frequency analysis device, a statistical evaluation device, a fundamental frequency modifier and a speech signal generator. The frequency analysis device is configured to determine an instantaneous fundamental frequency value of a speech signal for a time portion of the speech signal. The statistical evaluation device is configured to determine an average fundamental frequency value of the speech signal over several time portions. The fundamental frequency modifier is configured to modify the instantaneous fundamental frequency value to a modified fundamental frequency value such that a difference or a quotient of the instantaneous fundamental frequency value is changed to the average fundamental frequency value according to a specific function, in order to thus modify a frequency range within which the fundamental frequency value varies. The speech signal generator is configured to generate, on the basis of the modified fundamental frequency value, a speech signal modified with regard to the fundamental frequency.

Embodiments of the present invention are based on the realization that, due to the relatively coarse frequency resolution of hearing aids and particularly implantable auditory prostheses, perception of linguistic side information, such as prosody (among others, speech melody and emotions transferred therewith), is possible only to a very limited extent for users of such hearing aids. Particularly, it could be that a sentence spoken by a specific person is reproduced only through a small number of electrodes, as the language and particularly the fundamental frequency varies within a limited frequency range only, although a person with normal hearing may absolutely recognize a clear change in pitch. In contrast, due to the small number of electrodes used, especially a user of an implanted auditory prosthesis often has difficulties in detecting changes in pitch that, among others, are important for distinguishing between questions and statements and for recognizing sentence boundaries. To solve this, the present invention suggests extending the frequency range within which the fundamental frequency of a specific speaker varies, for example, in order to indicate questions, statements and sentence boundaries, refraining from a complex and often erroneous syntactical analysis of the speech signal. Thus, at least some embodiments of the present invention are also based on the additional or alternative realization that the actual difficulty of a hearing aid in everyday use is to perform a reliable syntactical analysis of a speech signal by means of computer-implemented algorithms, in order to subsequently perform a modification of the fundamental frequency. Contrary to these requirements of using a hearing aid in everyday life, scientific studies in this field have manually adapted the fundamental frequency of manually selected parts of sentences in order to have well-defined test data at one's disposal, on the one hand, and to examine the effect of a fundamental frequency variation on the capability of comprehension of hearing aid users, on the other hand. In contrast, the present invention now suggests increasing (amplifying) the pitch variations of the fundamental frequency that are present in the original speech signal, so that the range of variation of the fundamental frequency of a specific speaker is increased. Thus, the present invention solves the problem, among others, of how the hearing aid can determine which time portions of the speech signal should be modified with regard to their fundamental frequency and in which way (increasing the fundamental frequency, decreasing the fundamental frequency, substantially maintaining the fundamental frequency). The present invention does so by determining an average fundamental frequency for the current speaker and his/her current way of speaking (for example, neutral, quiet, excited, elated, indignant, etc.). This average fundamental frequency then serves as a reference frequency (like a "pivot") for modifying the fundamental frequency.

Modification of the fundamental frequency value serves to determine a modified fundamental frequency value. Said modification can be done by means of a function or (mathematical) mapping within which a difference between the instantaneous fundamental frequency value and the average fundamental frequency value is reflected as an argument. The function or (mathematical) mapping can be parameterizable by means of one or more parameters. As one example of a parameter, a pitch range factor (PRF) shall be mentioned, which indicates by how much the difference between the instantaneous fundamental frequency value and the average fundamental frequency is to be scaled or extended. Instead of the difference, a different relation between the instantaneous fundamental frequency value and the average fundamental frequency value, such as the quotient, is also possible.

According to some embodiments, the hearing aid apparatus may further include a device for classifying voiced time portions and unvoiced time portions, the frequency analysis device and the statistical evaluation device being configured to determine the instantaneous fundamental frequency value and the average fundamental frequency value by means of time portions of the speech signal that are classified as being voiced. In many cases, determining and changing the fundamental frequency only makes sense within voiced time portions of the speech signal, so that, by distinguishing between voiced and unvoiced time portions, a distortion in determining the instantaneous fundamental frequency value and the average fundamental frequency value, by voiced parts, can be largely avoided.

According to some embodiments, the frequency analysis device may be part of a device for linear predictive coding analysis (LPC), and the speech signal generator may be a device for linear predictive coding synthesis. Linear predictive coding rather realistically models natural generation of a speech signal by a human being. Within the context of linear predictive coding analysis, the fundamental frequency value is determined as one signal parameter of typically several signal parameters. In linear predictive coding synthesis, a speech signal, which substantially matches the original speech signal or at least does not differ too much from the original speech signal, is reproduced from the signal parameters. In doing so, the fundamental frequency is used to initially generate a so-called source signal. In some cases, also a residual signal is used for generating the source signal. Subsequently, the source signal is filtered, which involves modeling the corresponding filter (in accordance with the speaker's vocal tract, i.e., his/her throat and mouth area) by means of formant parameters. At the filter output, the speech signal reproduced in this manner (LPC-synthesized speech signal) is output. Since the fundamental frequency value is reflected, within the context of LPC analysis, in the synthesis independently of the formant parameters, a pitch change of the reproduced speech signal can be achieved by modifying the fundamental frequency value without substantially changing the formant frequencies and/or amplitudes of the reproduced speech signal. As the formant frequencies are not modified, especially vowels (a, e, i, o, u) and similar sounds remain understandable as usual. Furthermore, the voice still sounds natural, only the speech melody appears more pronounced.

According to some embodiments, the speech signal generator may be based on a Fast Fourier Transformation (FFT)

or PSOLA (pitch synchronous overlap and add). In principle, these methods offer the possibility of allowing the fundamental frequency to be reflected in the synthesis of the speech signal, independently of the formant frequencies, so that the fundamental frequency of the speech signal may be varied time portion by time portion without substantially distorting the formants.

According to some embodiments, the speech signal generator may be configured to not substantially change formant frequencies of the speech signal. As mentioned before, the comprehensibility especially of vowels and other voiced or partially voiced sounds is thus maintained.

According to some embodiments, the fundamental frequency modifier may be configured to keep an average modified fundamental frequency value substantially identical with the average fundamental frequency value. Thus, the hearing aid user still is provided with a benchmark for distinguishing between various speakers and their properties (male, female, or child). In other words, the hearing aid user substantially still has the possibility of distinguishing between sexes and identifying a speaker, which may be helpful for the hearing aid user in situations with two or more conversation partners.

According to some embodiments, the specific function by means of which the difference or quotient is changed may be a linear function having a proportionality factor (PRF), so that the difference or the quotient is scaled by means of the proportionality factor. Alternatively, other functions such as a sigmoid function are also possible.

According to some embodiments, the fundamental frequency modifier may be configured to limit the modified fundamental frequency value at at least one of a lower limit value and an upper limit value. In situations where the speaker already has a pronounced speech melody it is possible that the hearing aid user perceives enough information regarding prosody and emotions within the original speech signal even without modification of the fundamental frequency, and/or that unlimited modification of the fundamental frequency would lead to exaggerated variations of the pitch within the modified speech signal. Furthermore, limitation to the audible and/or technically feasible frequency range may be achieved in this manner, so that the modified fundamental frequency for example cannot fall below 50 Hz or even below 0 Hz.

According to some embodiments, the statistical evaluation device may be configured to determine temporal constancy of the fundamental frequency values of several time portions and to transmit the average fundamental frequency value to the fundamental frequency modifier only when the temporal constancy is above a minimum value. The temporal constancy, for example, may be expressed by a standard deviation of the fundamental frequency values as a minimum number of considered time portions (the higher the standard deviation, the lower the temporal constancy, and vice versa).

According to some embodiments, the hearing aid apparatus may further include a speaker change detector that is configured to detect when a change from a first speaker to another speaker has occurred within the speech signal, the statistical evaluation device and the fundamental frequency modifier being configured to interrupt data processing for the first speaker until the speaker change detector detects a change back to the first speaker. In an embodiment derived therefrom, a data memory for several speakers may be provided. The speaker change detector may be configured to identify a speaker stored in the data memory by means of characteristic properties (for example, fundamental frequency, formant frequencies, speech velocity (for example by the mean time interval between two voiced time portions) and, immediately after the identification, to continue data processing within the statistical evaluation device and the fundamental frequency modifier by using the values stored in the data memory—substantially without any delay.

Embodiments provide a method for processing a speech signal. The method includes determining an instantaneous fundamental frequency value of a speech signal for a time portion of the speech signal and determining an average fundamental frequency value of the speech signal over several time portions. The instantaneous fundamental frequency value is modified to a modified fundamental frequency value such that a difference or a quotient of the instantaneous fundamental frequency value is changed to the average fundamental frequency value according to a specific function, in order to modify a frequency range within which the fundamental frequency value varies. The method further includes generating, on the basis of the modified fundamental frequency value, a speech signal modified with regard to the fundamental frequency.

Embodiments provide a computer program for executing the method for processing a speech signal by means of a computer, processor, microcontroller or any other programmable signal processing apparatus.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
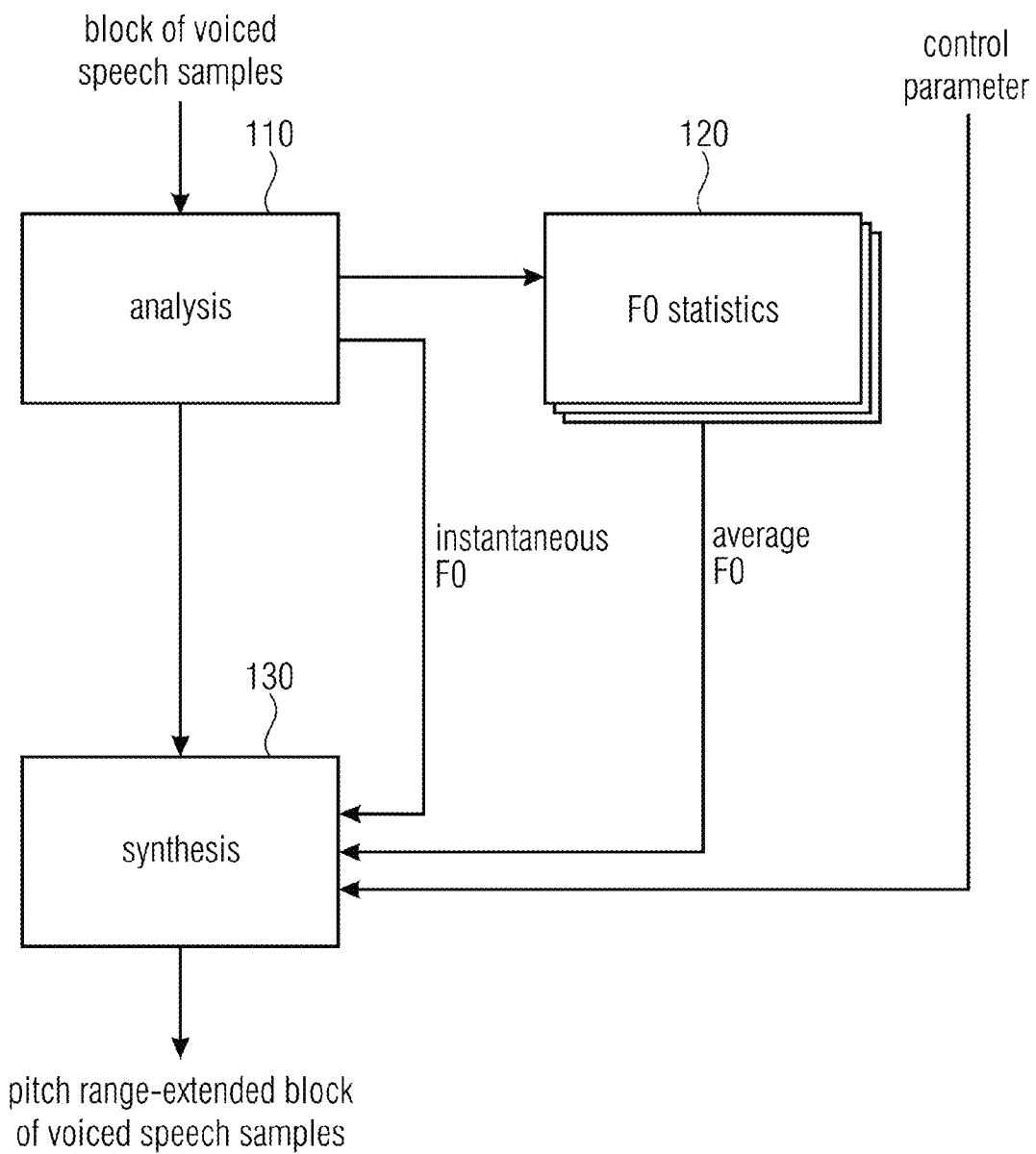
FIG. 1 is a schematic block diagram of a general overview of the suggested pitch range extender.

Before explaining embodiments of the present invention by means of the accompanying figures in detail, it should be noted that identical or equivalent elements or structures are provided with identical reference numerals, so that the descriptions thereof are mutually applicable and/or interchangeable.

In the context of this description and the claims, the term "hearing aid" denotes the generic term for technical apparatuses for improving the hearing capability of persons who are hard of hearing, or whose hearing is impaired. Within the group of hearing aids, the implantable auditory prostheses, among others, as well as the non-implantable auditory prostheses can be denoted as sub-groups. As mentioned above, within the sub-group of implantable auditory prostheses, the cochlear implants and the brain stem implants, among others, can be distinguished.

Currently, speech processors for hearing aids (especially for cochlear implants and brain stem implants) use a multitude of pre-processing algorithms including automatic gain and sensitivity control, optimization of the dynamic range, background noise reduction, wind noise reduction, etc. However, currently no pre-processing algorithm for improving prosodic indications and therefore for improving the perception of prosody is known. The method and the apparatus described herein fill this gap.

In linguistics, prosody includes the aspects of rhythm, accentuation and intonation of speech. While rhythm and accentuation are relatively well perceived by hearing-impaired listeners that are supported by hearing aids, auditory and audiological research begins to lay the specific focus on clarifying the reasons for poor intonation perception and its negative implications.

Acoustic features of intonation are encoded mainly in pitch variations. Embodiments of the present invention provide a method and an apparatus in order to:
improve acoustic features of intonation by increasing pitch variations,
in a manner that is to be included into the pre-processing chain of hearing aids,
which means that block-by-block processing of digitalized speech is possible,
and enables the listener to identify the sex and the speaker as the speaker's voice is not distorted or falsified,
this is achieved by changing the fundamental frequency F0 and its harmonics in a congruent way, and
by not significantly changing formant frequencies.

FIG. 1 shows a general overview of the suggested pitch range extender. A block of voiced speech samples serves as input data. This block represents a time portion of the speech signal created, for example, by a speaker and detected by a microphone of the hearing aid apparatus. Temporal sampling of the speech signal and subsequent analog-digital conversion can be performed in order to obtain a multitude of single digitalized speech samples.

The pitch range extender that can be part of a hearing aid apparatus includes an analysis device 110 that, in particular, can be a frequency analysis device. Said frequency analysis device 110 is configured to determine an instantaneous fundamental frequency value (instantaneous F0) of a speech signal for a time portion of the speech signal, the time portion herein corresponding to the block of voiced speech samples. However, other relations between a block of speech samples and a time portion are possible as well. The instantaneous fundamental frequency F0 is supplied to a statistical evaluation device 120 that is configured to determine an average fundamental frequency value F0* of the speech signal over several time portions. The instantaneous fundamental frequency value F0 and the average fundamental frequency value F0* are transmitted to a synthesis device or a speech signal generator 130 obtaining additional signal parameters regarding the speech signal from the frequency analysis device 110 as further input data. Based on the instantaneous fundamental frequency value F0, on the average fundamental frequency value F0* and on a control parameter, now a modified fundamental frequency is being determined. To this end, a difference or a quotient of the instantaneous fundamental frequency value F0 in relation to the average fundamental frequency value F0* is changed according to a specific predefined function in order to modify a frequency range within which the fundamental frequency value varies across a multitude of time portions. In this context, the control parameter defines an extent of the modification. The synthesis device 130 uses the modified fundamental frequency value for generating a modified speech signal within the corresponding time portion. Thus, the synthesis device 130 outputs, block by block in each case, a pitch range-extended block of voiced speech samples. In other words, the synthesis device 130 is configured to generate, on the basis of the modified fundamental frequency value, a speech signal modified with regard to the fundamental frequency.

Figure 2:
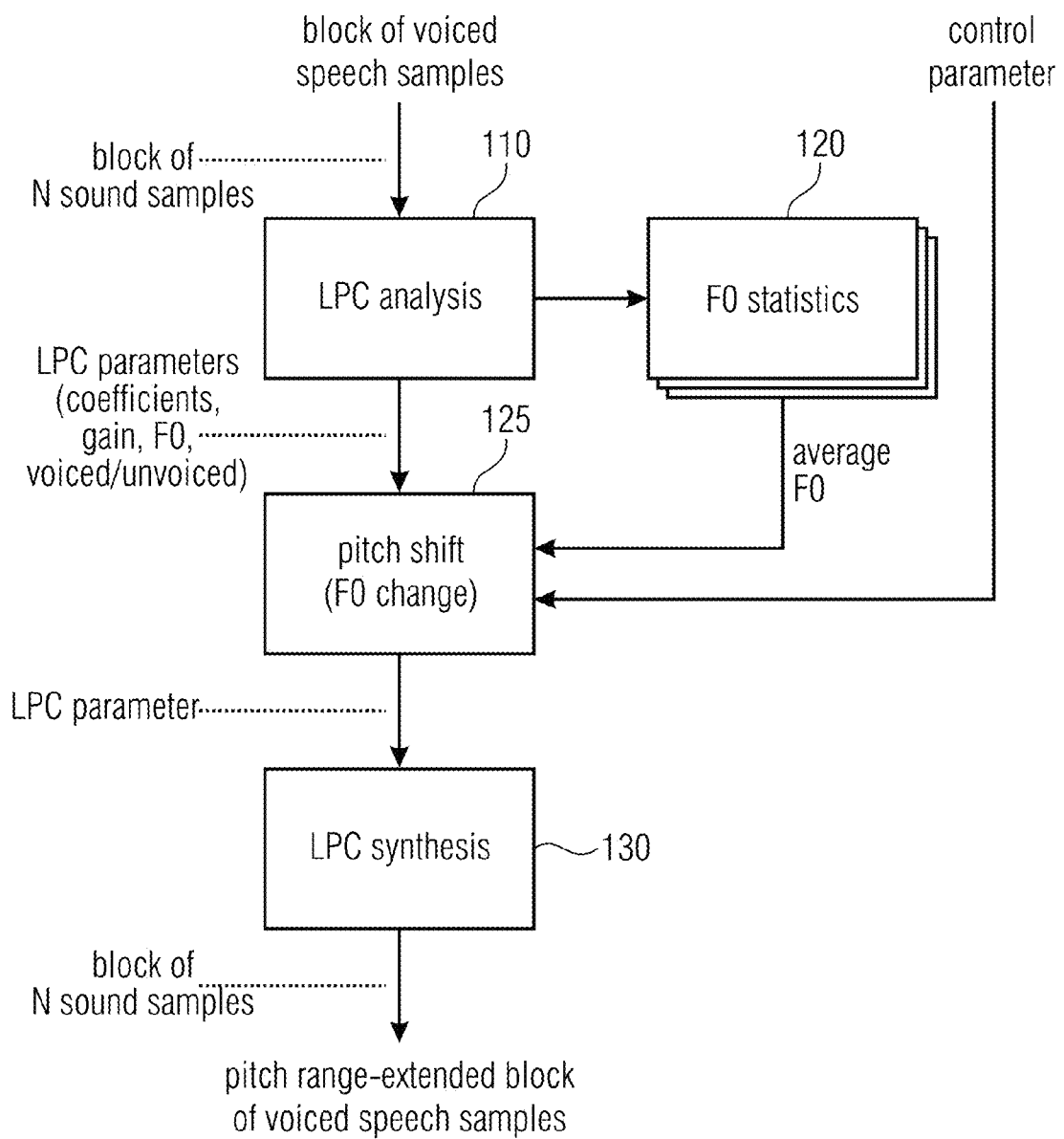
FIG. 2 is a schematic block diagram of an embodiment of the pitch range extender suggested herein that uses LPC (linear predictive coding)

FIG. 2 shows a schematic block diagram of an embodiment of the suggested method that uses linear predictive coding (LPC). As in FIG. 1, a block of voiced speech samples is analyzed by the frequency analysis device 110 in order to determine an instantaneous fundamental frequency value. For example, the block may have the size N, thus including N sound samples. The frequency analysis device 110 in FIG. 2 is an LPC analysis that also provides, besides the instantaneous fundamental frequency of the speech signal that is valid for the current block, a series of further LPC parameters, particularly: coefficients, gain, information regarding the voicing of the corresponding time portion or block of the speech signal. The LPC parameters are transmitted from the analysis device 110 to a fundamental frequency modifier 125 that performs a pitch shift or fundamental frequency change (F0 change). For this purpose, the fundamental frequency modifier 125 also obtains the average fundamental frequency value F0* from the statistical evaluation device 120. As in FIG. 1, at least one control parameter that sets the extent of the pitch range change is also provided. The LPC parameters including the modified fundamental frequency value are transmitted to the speech signal generator 130 that performs an LPC synthesis in the embodiment of FIG. 2. From the LPC parameters for the current block, the speech generator creates a block of N sound samples of the modified speech signal and/or the pitch range extended block of voiced speech symbols.

In the embodiment shown in FIG. 2, a block of digitalized sound samples is thus analyzed by the linear predictive coding technique. A set of coefficients, gain, fundamental frequency F0 and voiced/unvoiced parameters is determined for the short sound portion. Based on the instantaneous fundamental frequencies of consecutive blocks (of voiced signal parts), F0 statistics are built. In particular, an average fundamental frequency value (which may, for example, be the median) of the incoming sound is calculated that is indicated as F0*. The fundamental frequency modifier or the pitch shift unit 125 also maintains an average F0 (for example indicated as F0**) of already processed data. The pitch range is extended in such a manner that the average of the fundamental frequency remains approximately the same, that is F0*≈F0**, but the difference between F0* and the instantaneous fundamental frequency F0 is scaled according to the PRF factor. PRF=100%, therefore, means that there is no change, whereas PRF=200% means that the F0 range (maximum F0−minimum F0) doubles. High PRF values may entail the restriction or limitation of the minimum possible and/or maximum possible F0. Furthermore, one might build F0 statistics first (over up to several hundreds of milliseconds) without actually changing the pitch. If need be, the system can be extended in such a way that it bypasses processing (particularly the change of the fundamental frequency and the update of the statistics) when several speakers are speaking at the same time. Another possible extension of the system may consist in the system detecting sudden changes of speakers.

Instead of LPC (as shown in FIG. 2), different formant-preserving pitch change methods may be used. These may be based on FFT (Fast Fourier Transform), PSOLA (pitch synchronous overlap and add) or other techniques.

Figure 3:
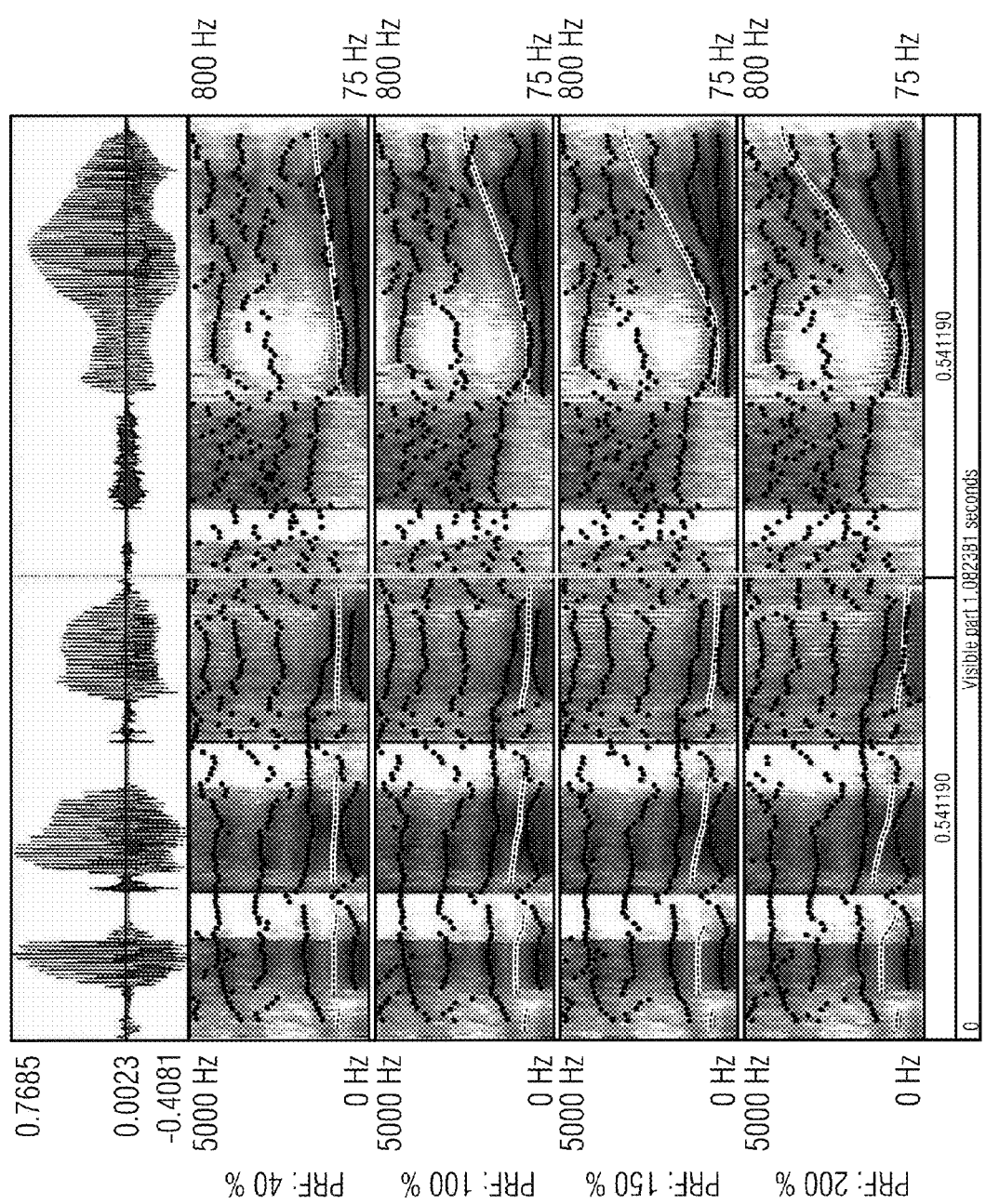
FIG. 3 is a chronological sequence of a speech signal and several spectrograms of the speech signal as well as of the modified speech signal for different values of the pitch range factor PRF.

In the embodiments according to FIGS. 1 and 2, the control parameter specifies the extent of extension of the pitch range as exemplarily represented in FIG. 3. The control parameter may be a pitch range factor PRF, for example.

In the upper part FIG. 3 shows the temporal wave form of a speech signal representing the short German sentence "Britta kauft Schuhe?" ("Britta is buying shoes?") that was intoned as a question (fundamental frequency rises towards the last syllable). The four lower sub-diagrams show spectrograms of the linguistic expression after processing using different values for the pitch range factor PRF as control parameters, in particular PRF=40% (reduction of the pitch range of the fundamental frequency), PRF=100% (no change of the original speech signal), PRF=150% (moderate increase of the pitch range of the fundamental frequency) and PRF=200% (significant increase of the pitch range of the fundamental frequency). The progressions of the formant frequencies are indicated by black dots. For the spectrograms and the formant frequencies the left-hand frequency scale from 0 Hz to 5000 Hz is valid. The progressions of the fundamental frequencies are indicated by white lines (right-hand frequency scale from 75 Hz to 800 Hz). The progression of the fundamental frequency is shown only for time portions that have been classified as voiced. For time portions classified as unvoiced, no progression of the fundamental frequency is shown.

FIG. 3 clearly shows that, particularly in cases where PRF=150% and PRF=200%, the fundamental frequency clearly increases more strongly towards the end of the sentence than in the unchanged case of PRF=100%. Thereby, a person with a hearing aid is able to more easily recognize that the present sentence is a question. In FIG. 3, it is also apparent that the formant frequencies represented by the black dots are almost unchanged.

Based on a previous clinical study and first self-experiments of the inventor, a significant improvement of the perception of intonation can be expected for speech signals that are processed according to the suggested method. The clinical study mentioned used manually processed speech signals wherein specific words or syllables were manually changed regarding their pitch. For someone performing the manual change, it is no problem to mark the corresponding word in a graphically represented signal wave form and to subject said signal portion to linear predictive coding with a modified fundamental frequency if said person knows the corresponding language (German, English, Chinese, Japanese, etc.) and has basic knowledge in audio signal processing. For manual processing, the person in question uses his/her knowledge of the semantics and syntax of the corresponding language, in particular. For the application in a hearing aid, however, it is desirable to do without the high computing expenditure and the high requirements placed on stored data or the data amount that would accompany a computer-aided semantic and syntax analysis. Furthermore, a computer-aided semantics and syntax analysis for each language (German, English, etc.) would necessitate the execution of a different program or at least the loading of a different configuration which, on the one hand, may be bothersome for the person with the hearing aid and, on the other hand, means that a large amount of effort is involved in programming and training people in semantic and syntax analysis. The suggested invention, however, may be used universally and independently of the language of the speaker, reliably delivers the desired result and necessitates only little additional signal processing effort within the hearing aid.

Figure 4:
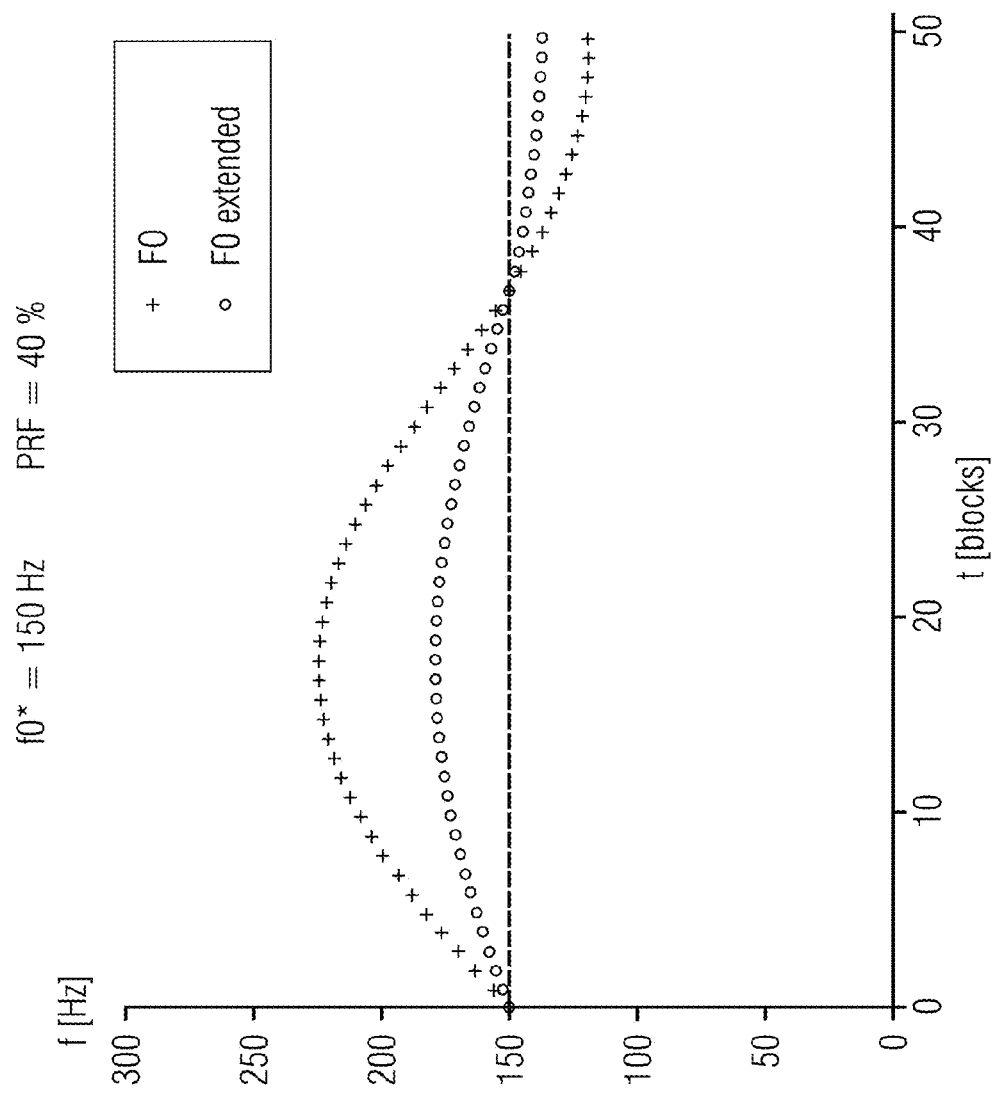
FIG. 4 is a schematic sequence of a fundamental frequency and a modified fundamental frequency for linear pitch range scaling with the pitch range factor PRF=40% (in fact, a decrease of the pitch range)
Figure 5:
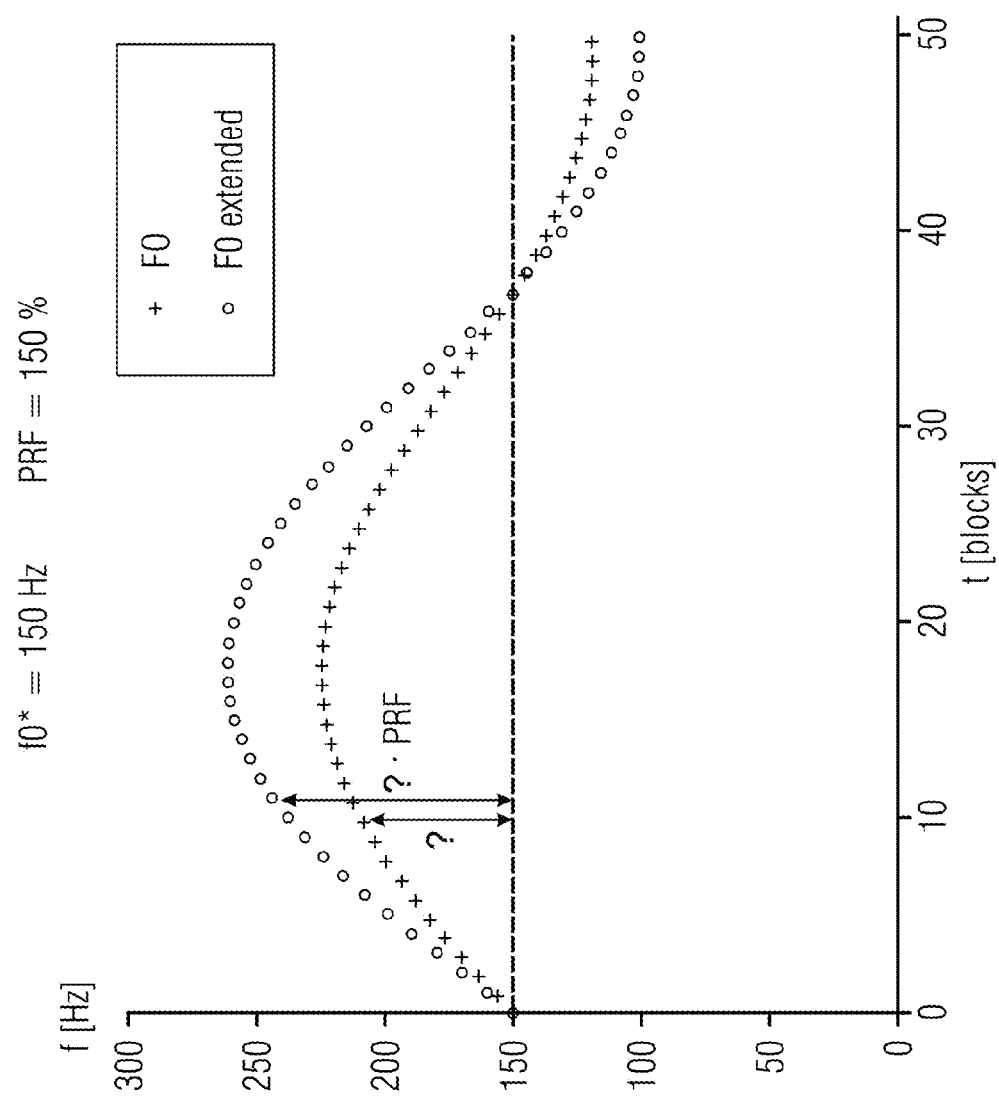
FIG. 5 is a schematic sequence of a fundamental frequency and a modified fundamental frequency for linear pitch range scaling with the pitch range factor PRF=150%.
Figure 6:
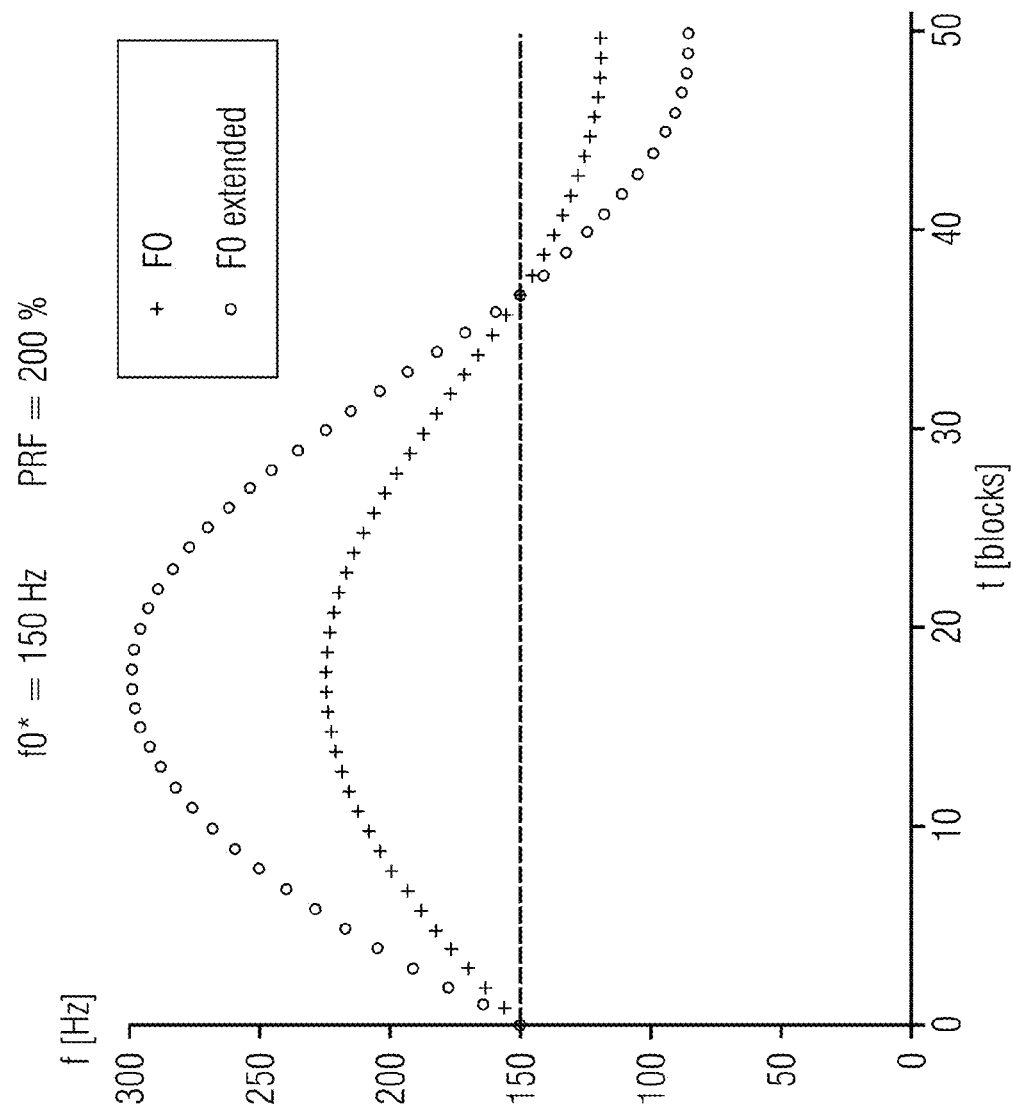
FIG. 6 is a schematic sequence of a fundamental frequency and a modified fundamental frequency for linear pitch range scaling with the pitch range factor PRF=200%.

FIGS. 4 to 6 schematically show the modification of the original fundamental frequency F0 to the modified fundamental frequency F0* for the PRF values 40%, 150% and 200%. The figures each show 50 blocks on the time axis. Each block may include N samples. In all cases that are represented in FIGS. 4 to 6, the average fundamental frequency is constantly at 150 Hz and is represented as a dotted line. It is to be noted that determining the average fundamental frequency might be implemented as a moving average, for example, so that the average fundamental frequency may (slightly) change from one block to the next.

In FIG. 5, the difference $\Delta=F0-F0*$ and the modified difference $\Delta \cdot PRF=(F0-F0*) \cdot PRF$ is graphically represented for illustrative purposes. Instead of the difference, a different relation between the instantaneous fundamental frequency F0 and the average fundamental frequency F0* may also be used, for example the quotient F0/F0*.

Figure 7:
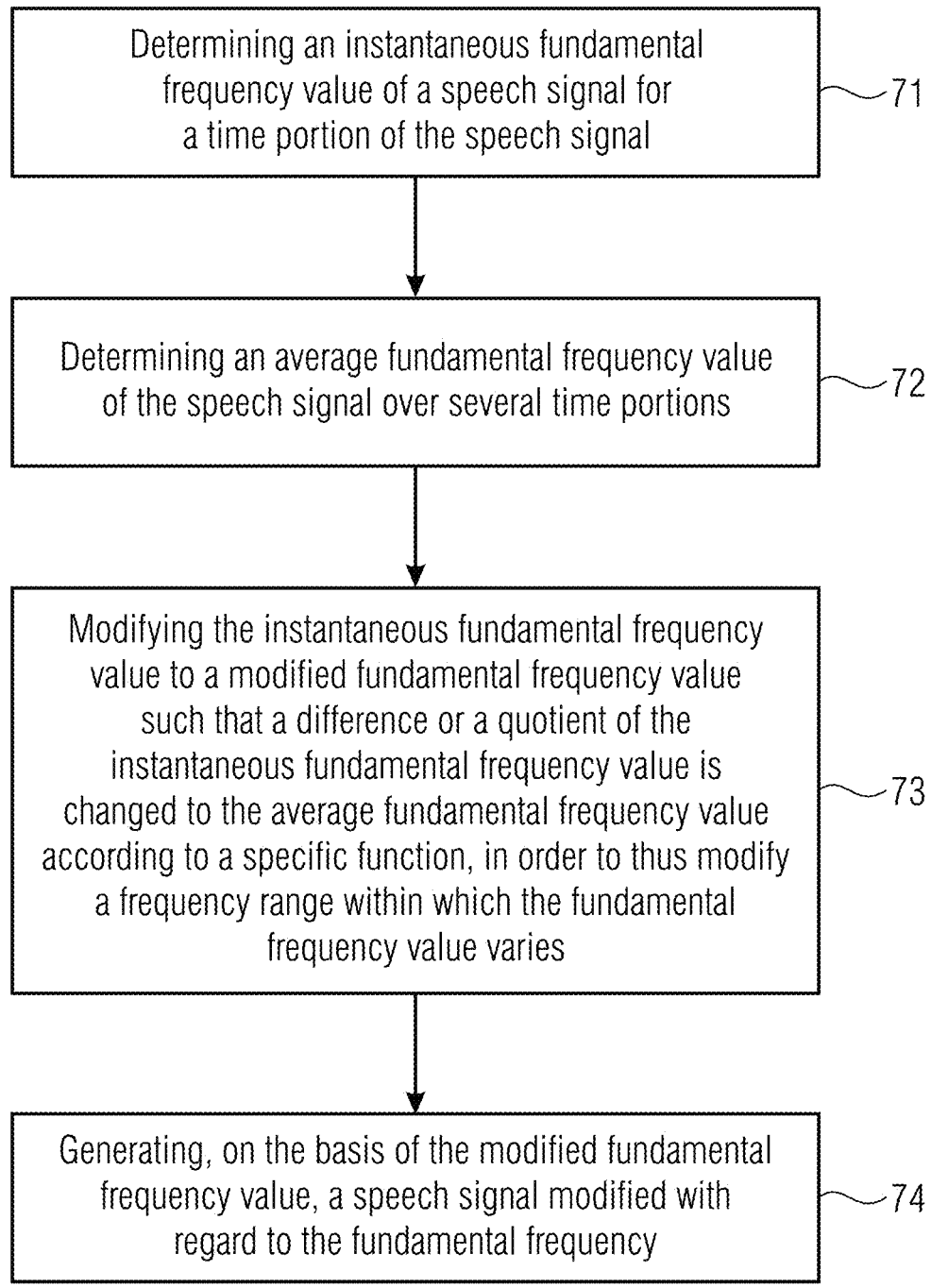
FIG. 7 is a schematic flow chart of a method for processing a speech signal according to an embodiment.

FIG. 7 shows a schematic flow chart of a method for processing a speech signal according to embodiments of the present invention. In a step 71, an instantaneous fundamental frequency value F0 of a speech signal is determined for a time portion of the speech signal. In a subsequent step 72, an average fundamental frequency value F0* of the speech signal is determined over several time portions. The instantaneous fundamental frequency value F0 then is modified to a modified fundamental frequency value in a step 73. For this purpose, a difference or a quotient of the instantaneous fundamental frequency value F0 in relation to the average fundamental frequency value F0*, for example, is changed according to a specific function. Thereby, a frequency range (particularly the width of the frequency range) within which the fundamental frequency value varies may be modified. In a step 74, a speech signal modified with regard to the fundamental frequency is generated on the basis of a modified fundamental frequency value.

According to further embodiments, the method may include a classification of voiced time portions and unvoiced time portions, said determining of the instantaneous fundamental frequency value and the average fundamental frequency value having to be performed by means of time portions of the speech signal that have been classified as voiced. The time portions that have been classified as unvoiced, however, usually are not used for determining the instantaneous fundamental frequency value and the average fundamental frequency value.

Determining the instantaneous fundamental frequency value may be performed within the context of a linear predictive coding analysis (LPC). Generating the modified speech signal may be performed according to a linear predictive coding synthesis, use being made of the modified fundamental frequency value. According to alternative embodiments thereof, generating the modified speech signal may be based on a Fast Fourier Transformation or PSOLA (pitch synchronous overlap and add).

According to embodiments, formant frequencies of the speech signal essentially are not changed. Typically, this pertains mainly to generating the modified speech signal.

According to embodiments, during the step of modifying the instantaneous fundamental frequency value care can be taken to ensure that an average modified fundamental frequency value is kept substantially identical with the average fundamental frequency value.

The specific function by means of which the difference or the quotient is changed can be, for example, a linear function with a proportionality factor (PRF), so that the difference or the quotient is scaled by means of the proportionality factor.

According to embodiments, the modified fundamental frequency value may be limited at at least one of a lower limit value and an upper limit value in order to prevent an excessive or exaggerated change of the fundamental frequency.

According to embodiments, the method may further include determining temporal constancy of the fundamental frequency values within several time portions. Only when the temporal constancy is above a preset (configured) minimum value will the instantaneous fundamental frequency value be modified on the basis of the average fundamental frequency value. Thereby, it can be prevented that, for example in case of a change of speaker, transition effects influence the modification of the fundamental frequency value in an undesired manner.

According to further possible embodiments, the method may include a step for detecting a change of speaker. Thus, it is possible to detect when a change from a first speaker to another speaker has occurred within the speech signal. Determining the average fundamental frequency and modifying the instantaneous fundamental frequency value for the first speaker may be interrupted until another change of speaker, back to the first speaker, is detected.

Even though some aspects have been described within the context of a device, it is understood that said aspects also represent a description of the corresponding method, so that a block or a structural component of a device is also to be understood as a corresponding method step or as a feature of a method step. By analogy therewith, aspects that have been described within the context of or as a method step also represent a description of a corresponding block or detail or feature of a corresponding device. Some or all of the method steps may be performed by a hardware device (or while using a hardware device), such as a microprocessor, a programmable computer or an electronic circuit. In some embodiments, some or several of the most important method steps may be performed by such a device.

Some embodiments in accordance with the invention thus comprise a data carrier which comprises electronically readable control signals that are capable of cooperating with a programmable computer system such that any of the methods described herein is performed.

Generally, embodiments of the present invention may be implemented as a computer program product having a program code, the program code being effective to perform any of the methods when the computer program product runs on a computer.

The program code may also be stored on a machine-readable carrier, for example.

Other embodiments include the computer program for performing any of the methods described herein, said computer program being stored on a machine-readable carrier.

In other words, an embodiment of the inventive method thus is a computer program which has a program code for performing any of the methods described herein, when the computer program runs on a computer.

A further embodiment of the inventive methods thus is a data carrier (or a digital storage medium or a computer-readable medium) on which the computer program for performing any of the methods described herein is recorded.

A further embodiment of the inventive method thus is a data stream or a sequence of signals representing the computer program for performing any of the methods described herein. The data stream or the sequence of signals may be configured, for example, to be transferred via a data communication link, for example via the internet.

A further embodiment includes a processing means, for example a computer or a programmable logic device, configured or adapted to perform any of the methods described herein.

A further embodiment includes a computer on which the computer program for performing any of the methods described herein is installed.

A further embodiment in accordance with the invention includes a device or a system configured to transmit a computer program for performing at least one of the methods described herein to a receiver. The transmission may be electronic or optical, for example. The receiver may be a computer, a mobile device, a memory device or a similar device, for example. The device or the system may include a file server for transmitting the computer program to the receiver, for example.

In some embodiments, a programmable logic device (for example a field-programmable gate array, an FPGA) may be used for performing some or all of the functionalities of the methods described herein. In some embodiments, a field-programmable gate array may cooperate with a microprocessor to perform any of the methods described herein. Generally, the methods are performed, in some embodiments, by any hardware device. Said hardware device may be any universally applicable hardware such as a computer processor (CPU), or may be a hardware device specific to the method, such as an ASIC.

While this invention has been described in terms of several embodiments, there are alterations, permutations, and equivalents which fall within the scope of this invention. It should also be noted that there are many alternative ways of implementing the methods and compositions of the present invention. It is, therefore, intended that the following appended claims be interpreted as including all such alterations, permutations and equivalents as fall within the true spirit and scope of the present invention.

The invention claimed is:

1. A hearing aid apparatus, comprising:
    a frequency analysis device that is configured to determine an instantaneous fundamental frequency value of a speech signal for a time portion of the speech signal;
    a statistical evaluation device that is configured to determine an average fundamental frequency value of the speech signal over several time portions;
    a fundamental frequency modifier that is configured to modify the instantaneous fundamental frequency value to a modified fundamental frequency value such that a difference between the instantaneous fundamental frequency value and the average fundamental frequency value or a quotient between the instantaneous fundamental frequency value and the average fundamental frequency value is changed according to a specific function, in order to thus modify a frequency range within which the fundamental frequency value varies;
    a speech signal generator that is configured to generate, on the basis of the modified fundamental frequency value, a speech signal modified with regard to the fundamental frequency, and
    the hearing aid configured to output the speech signal as sound.

2. The hearing aid apparatus according to claim 1, further comprising a device for classifying voiced time portions and unvoiced time portions, the frequency analysis device and the statistical evaluation device being configured to determine the instantaneous fundamental frequency value and the average fundamental frequency value by means of time portions of the speech signal that are classified as voiced.

3. The hearing aid apparatus according to claim 1, wherein the speech signal generator is configured to not substantially change formant frequencies of the speech signal.

4. The hearing aid apparatus according to claim 1, wherein the fundamental frequency modifier is configured to keep an average modified fundamental frequency value substantially identical with the average fundamental frequency value.

5. The hearing aid apparatus according to claim 1, wherein the frequency analysis device is part of a device for linear predictive coding analysis (LPC) and the speech signal generator is a device for linear predictive coding synthesis.

6. The hearing aid apparatus according to claim 1, wherein the speech signal generator is based on a Fast Fourier Transformation or PSOLA (pitch synchronous overlap and add).

7. The hearing aid apparatus according to claim 1, wherein the specific function by means of which the difference or the quotient is changed is a linear function comprising a proportionality factor (PRF), so that the difference or the quotient is scaled by means of the proportionality factor.

8. The hearing aid apparatus according to claim 1, wherein the fundamental frequency modifier is configured to limit the modified fundamental frequency value at at least one of a lower limit value and an upper limit value.

9. The hearing aid apparatus according to claim 1, wherein the statistical evaluation device is configured to determine a temporal constancy of the fundamental frequency values of several time portions and to transmit the average fundamental frequency value to the fundamental frequency modifier only when the temporal constancy is above a minimum value.

10. The hearing aid apparatus according to claim 1, further comprising a speaker change detector that is configured to detect when a change from a first speaker to another speaker has occurred within the speech signal, the statistical evaluation device and the fundamental frequency modifier being configured to interrupt data processing for the first speaker until the speaker change detector detects a change back to the first speaker.

11. A method for processing a speech signal, comprising:
determining an instantaneous fundamental frequency value of a speech signal for a time portion of the speech signal;
determining an average fundamental frequency value of the speech signal over several time portions;
modifying the instantaneous fundamental frequency value to a modified fundamental frequency value such that a difference between the instantaneous fundamental frequency value and the average fundamental frequency value or a quotient between the instantaneous fundamental frequency value and the average fundamental frequency value is changed according to a specific function in order to modify a frequency range within which the fundamental frequency value varies;
generating, on the basis of the modified fundamental frequency value, a speech signal modified with regard to the fundamental frequency, and
outputting the speech signal with a hearing aid.

12. A non-transitory digital storage medium having a computer program stored thereon to perform a method for processing a speech signal, said method comprising:
determining an instantaneous fundamental frequency value of a speech signal for a time portion of the speech signal;
determining an average fundamental frequency value of the speech signal over several time portions;
modifying the instantaneous fundamental frequency value to a modified fundamental frequency value such that a difference between the instantaneous fundamental frequency value and the average fundamental frequency value or a quotient between the instantaneous fundamental frequency value and the average fundamental frequency value is changed according to a specific function in order to modify a frequency range within which the fundamental frequency value varies; and
generating, on the basis of the modified fundamental frequency value, a speech signal modified with regard to the fundamental frequency,
outputting the speech signal with a hearing aid;
when said computer program is run by a computer.

* * * * *